United States Patent [19]

Alker et al.

[11] Patent Number: 4,590,195

[45] Date of Patent: May 20, 1986

[54] 4-ARYL-3,5-BIS(ALKOXYCARBONYL)-6-METHYL-2-AMINOALKYLOXYMETHYL-1,4-DIHYDROPYRIDINE ANTIHYPERTENSIVE AGENTS

[75] Inventors: David Alker, Eastry, Nr. Deal; Peter E. Cross, Canterbury; Simon F. Campbell, Deal, all of England

[73] Assignee: Pfizer Inc., New York, N.Y.

[21] Appl. No.: 586,514

[22] Filed: Mar. 5, 1984

[30] Foreign Application Priority Data

Mar. 10, 1983 [GB] United Kingdom ............... 8306666

[51] Int. Cl.$^4$ ............... C07D 401/12; C07D 211/82; C07D 213/55; A61K 31/495; A61K 31/44

[52] U.S. Cl. ............................. 514/252; 544/364; 544/124; 544/310; 544/336; 546/255; 546/153; 546/193; 546/256; 546/261; 546/262; 546/270; 546/271; 546/274; 546/278; 546/280; 546/282; 546/283; 546/340; 546/341; 514/256; 514/314; 514/318; 514/332; 514/333; 514/335; 514/336; 514/338; 514/339; 514/341; 514/342; 514/343; 514/356

[58] Field of Search ............... 546/256, 261, 262, 270, 546/271, 274, 278, 280, 282, 283, 340, 341; 424/263; 544/364; 514/252

[56] References Cited

U.S. PATENT DOCUMENTS 3,974,278  8/1976  Bossert et al. .................. 546/262
4,380,547  4/1983  Materne ......................... 546/270
4,430,333  2/1984  Campbell et al. ................ 424/266

FOREIGN PATENT DOCUMENTS 0031801  7/1981  European Pat. Off.
0060674  9/1982  European Pat. Off.
0089167  9/1983  European Pat. Off.
55-47656  4/1980  Japan.
1585978  3/1981  United Kingdom.

Primary Examiner—George F. Lesmes
Assistant Examiner—S. A. Gibson
Attorney, Agent, or Firm—Charles J. Knuth; Albert E. Frost; James M. McManus

[57] ABSTRACT 1,4-Dihydropyridine derivatives of the formula:

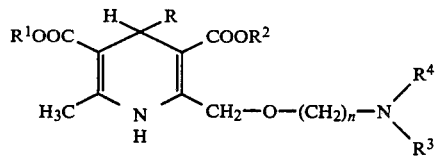

wherein R is aryl or heteroaryl; $R^1$ and $R^2$ are each $C_1$-$C_4$ alkyl or 2-methoxyethyl; n is 2, 3 or 4; $R^3$ is H, $C_1$-$C_4$ alkyl, $CH_2CO_2(C_1$-$C_4$ alkyl) or $CH_2CN$; and $R^4$ is a group of the formula $COR^5$, $CSR^5$, $C(=NR^6)R^7$ or $SO_2R^5$, wherein $R^5$ is $C_1$-$C_4$ alkyl, $NH_2$, $NH(C_1$-$C_4$ alkyl), $NH(C_3$-$C_6$ cycloalkyl), $N(C_1$-$C_4$ alkyl)$_2$, $NHCH_2CO_2(C_1$-$C_4$ alkyl), $NHCH_2CONH_2$, $NHCH_2CO_2H$, $NH(CH_2)_2NH_2$, $NHNH_2$, $NHNRCO_2$(-$C_1$-$C_4$ alkyl), NH-aryl, NHCO-aryl or a heterocyclic, NH-heterocyclic or NHCO-heterocyclic group, or when $R^4$ is $C(=O)R^5$, $R^5$ may be H or $CF_3$; $R^6$ is H, CN, $CO_2(C_1$-$C_4$ alkyl), $CO(C_1$-$C_4$ alkyl), $SO_2(C_1$-$C_4$ alkyl), $SO_2$-aryl, $SO_2NH_2$, $SO_2N(C_1$-$C_4$ alkyl)$_2$, $NO_2$ or aryl; and $R^7$ is $NH_2$, $NH(C_1$-$C_4$ alkyl), $NHCO(C_1$-$C_4$ alkyl), $NH(CH_2)_mN(C_1$-$C_4$ alkyl)$_2$ wherein m is 2 to 4 or a NH-heterocyclic group; and their pharmaceutically acceptable acid addition salts, and pharmaceutical preparation containing such compounds, have utility as anti-ischaemic and antihypertensive agents.

6 Claims, No Drawings

4-ARYL-3,5-BIS(ALKOXYCARBONYL)-6-METHYL-2-AMINOALKYLOXYMETHYL-1,4-DIHYDROPYRIDINE ANTIHYPERTENSIVE AGENTS

BACKGROUND OF THE INVENTION

This invention relates to certain dihydropyridines, specifically to certain 1,4-dihydropyridines having a nitrogen containing group in a side chain attached to the 2-position, which have utility as anti-ischaemic and antihypertensive agents, and to pharmaceutical preparations containing such compounds.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

BRIEF DESCRIPTION OF THE INVENTION

According to the invention, there are provided novel 1,4-dihydropyridine derivatives of the formula:

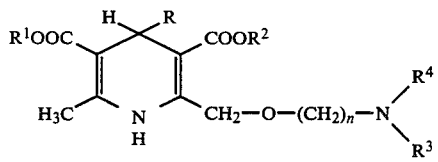

wherein
R is aryl or heteroaryl;
$R^1$ and $R^2$ are each independently $C_1$–$C_4$ alkyl or 2-methoxyethyl;
n is 2, 3 or 4;
$R^3$ is H, $C_1$–$C_4$ alkyl, $CH_2CO_2(C_1$–$C_4$ alkyl) or $CH_2CN$; and
$R^4$ is a group of the formula:

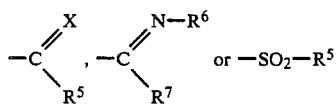

wherein
X is O or S;
$R^5$ is $C_1$–$C_4$ alkyl, $NH_2$, $NH(C_1$–$C_4$ alkyl), $NH(C_3$–$C_6$ cycloalkyl), $N(C_1$–$C_4$ alkyl)$_2$, $NHCH_2CO_2(C_1$–$C_4$ alkyl), $NHCH_2CONH_2$, $NHCH_2CO_2H$, $NH(CH_2)_2NH_2$, NH $NH_2$, $NHNRCO_2(C_1$–$C_4$ alkyl)$, NH-aryl, NHCO-aryl, or a heterocyclic, NH-heterocyclic or NHCO-heterocyclic group or when $R^4$ is C(=O)$R^5$, $R^5$ may be H or $CF_3$;

$R^6$ is H, CN, $CO_2(C_1$–$C_4$ alkyl), $CO(C_1$–$C_4$ alkyl), $SO_2(C_1$–$C_4$ alkyl), $SO_2$-aryl, $SO_2NH_2$, $SO_2N(C_1$–$C_4$ alkyl)$_2$, $NO_2$ or aryl; and
$R^7$ is $NH_2$, $NH(C_1$–$C_4$ alkyl), $NHCO(C_1$–$C_4$ alkyl), $NR(CM_2)_mN(C_1$–$C_4$ alkyl)$_2$ wherein m is 2 to 4 or a NH-heterocyclic group;
and their pharmaceutically acceptable acid addition salts.

The compounds of the formula (I) containing one or more asymmetric centres will exist as one or more pairs of enantiomers, and such pairs or individual isomers may be separable by physical methods, e.g. by fractional crystallisation of the free bases or suitable salts or chromatography of the free bases. The invention includes the separated pairs as well as mixtures thereof, as racemic mixtures or as separated d- and l-optically-active isomeric forms.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts.

The term "aryl" as used in this specification, includes phenyl and phenyl substituted by one or two substituents selected from nitro, halo, $C_1$–$C_4$ alkyl, $C_1$–$C_4$ alkoxy, hydroxy, trifluoromethyl, and cyano. It also includes 1- and 2-naphthyl.

The term "heteroaryl" as used in this specification means an aromatic heterocyclic group which may optionally be substituted and includes, for example, benzofuranyl; benzothienyl; pyridyl optionally monosubstituted by methyl, thiomethyl, halo or cyano; quinolyl; benzoxazolyl; benzthiazolyl; furyl; pyrimidinyl; thiazolyl; 2,1,3-benzoxadiazol-4-yl; 2,1,3-benzthiadiazol-4-yl; and thienyl optionally monosubstituted by halo or $C_1$–$C_4$ alkyl.

The term "heterocyclic group" used in connection with $R^5$ and $R^7$ means a 5 or 6 membered nitrogen, oxygen, or sulphur containing heterocyclic group which may be saturated or unsaturated and which may optionally include a further one or two nitrogen atoms in the ring and which may optionally be benzofused or substituted with for example, halo, $C_1$–$C_4$ alkyl, hydroxy, acetamido, carbamoyl oxo or $NR^{13}R^{14}$ groups where $R^{13}$ and $R^{14}$ are each independently H, $C_1$–$C_4$ alkyl or $C_3$–$C_6$ cycloalkyl or, together with the nitrogen atom to which they are attached, they form a 5 or 6 membered saturated heterocyclic ring optionally containing a further oxygen atom or NH or N($C_1$–$C_4$ alkyl) group. Particularly suitable examples include pyridyl, pyrazinyl, hydroxypyridyl, dihydroxypyrimidinyl, piperidinyl, piperazinyl, 4-methyl-1-piperazinyl, morpholinyl, 1-imidazolidin-2-one, 2-furyl, thienyl, thiazolyl and quinolyl.

"Halo" means fluoro, chloro, bromo or iodo.

Alkyl and alkoxy groups having 3 or more carbon atoms can be straight or branched chain.

R is preferably 2-chlorophenyl or 2,3-dichlorophenyl. $R^1$ and $R^2$ are preferably $CH_3$ or $C_2H_5$, especially when $R^1$ is $CH_3$ and $R^2$ is $C_2H_5$. n is preferably 2. $R^3$ is preferably H or $CH_3$.

Preferred groups for $R^4$ are $COR^5$ where $R^5$ is H, $NHCH_3$, $NHCH_2CONH_2$ or 2-pyridon-5-yl; $CSR^5$ where $R^5$ is $NH_2$; $C(=NR^6)R^7$ where $R^6$ is CN and $R^7$ is $NHCH_3$; and $SO_2R^5$ where $R^5$ is $NH_2$, $NHCH_3$, NH

DETAILED DESCRIPTION OF THE INVENTION

The compounds of the formula (I) are prepared by a number of different processes according to the invention as follows:

(a) The ureas and thioureas of formula (I) wherein $R^4$ is $—C(=X)R^5$, X is O or S and $R^5$ is $NH_2$, $NH(C_1–C_4$ alkyl), $NH(C_3–C_6$ cycloalkyl), $NHCH_2CO_2(C_1–C_4$ alkyl), NH-aryl, NHCO-aryl, or a NH-heterocyclic or NHCO-heterocyclic group are prepared from an amine of the formula:

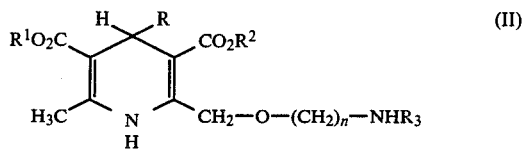

wherein R, $R^1$, $R^2$, $R^3$ and n are as previously defined by reacting with potassium cyanate or with an isocyanate or isothiocyanate of the formula:

$$R^8NCX \qquad (III)$$

wherein X is O or S and $R^8$ is $C_1–C_4$ lower alkyl, $C_3–C_6$ cycloalkyl, $CH_2CO_2(C_1–C_4$ alkyl), aryl, CO-aryl, or a heterocyclic or CO-heterocyclic group, respectively.

The reaction is simply performed by stirring the reactants together in a reaction-inert organic solvent at room temperature for several hours.

Compounds of the formula I wherein $R^4$ is $—C(=X)R^5$ and $R^5$ is $NHCH_2CONH_2$ or $NHCH_2CO_2H$ are readily prepared from the compound wherein $R^5$ is $NHCH_2CO_2(C_1–C_4$ alkyl) by reacting with concentrated ammonium hydroxide to yield the corresponding amides or by hydrolysing, for example with dilute sodium hydroxide, to yield the corresponding acids.

The urea derivatives wherein $R^4$ is $C(=X)R^5$, X is O and $R^5$ is $NH_2$ are prepared in a similar manner to that described above from the amine (II) but using potassium cyanate.

(b) The thiourea derivatives wherein $R^4$ is $—C(=S)R^5$ and $R^5$ is $NH_2$, $NH(C_1–C_4$ alkyl), $NH(C_3–C_6$ cycloalkyl) or $N(C_1–C_4$ alkyl)$_2$ are prepared by first reacting the amines of formula (II) with rhiophosgene and reacting the resulting isothiocyanate intermediates with ammonia or with a $(C_1–C_4)$ alkylamine, $(C_3–C_8)$cycloalkylamine or (di-$C_1–C_4$) alkylamine respectively.

The reaction of the amine (II) and thiophosgene is conveniently performed by adding thiophosgene to a stirred solution of the amine in a mixture of water and methylene chloride in the presence of powdered calcium carbonate. After several hours at room temperature the organic layer containing the isothiocyanate intermediate is separated and the product isolated. This is then heated with ethanolic ammonia solution or with the appropriate amine to yield the thiourea product.

(c) In an alternative process, urea derivatives of formula (I) wherein $R^4$ is $C(=X)R^5$, X is O and $R^5$ is $NHCH_2CONH_2$, $NHCH_2CH_2NH_2$, NH-heterocyclic, $NHNH_2$ or $NHNHCO_2CH_2CH_3$ are prepared from an amine of formula (II) by first reacting with $N,N^1$-carbonyldiimidazole and reacting the resulting imidazolylcarbonyl derivative with an amine or hydrazine derivative of formula $NH_2CH_2CONH_2$, $NH_2CH_2CH_2NH_2$, $NH_2$-heterocyclic, $NH_2NH_2$ or $NH_2NHCO_2CH_2CH_3$, respectively.

(d) The amides of formula (I) wherein $R^4$ is $C(=X)R^5$, X is O and $R^5$ is H, $CF_3$, $C_1–C_4$ alkyl, or a heterocyclic group are also prepared from the amines of formula (II) by reacting with an acid of formula $R^9CO_2H$, or with an anhydride, acid chloride or activated derivative thereof, wherein $R^9$ is H, $CF_3$, $C_1–C_4$ alkyl or a heterocyclic group respectively.

Thus, compounds wherein $R^5$ is H ($R^4$ is formyl) are prepared by a conventional formylation reaction, for example, using a mixture of formic acid and acetic anhydride. Compounds wherein $R^5$ is $CF_3$ or $C_1–C_4$ alkyl are similarly conveniently prepared using the appropriate acid anhydride in pyridine. The compounds wherein $R^5$ is a heterocyclic group are rather more conveniently prepared from the appropriate carboxy-substituted heterocyclic group by a coupling reaction, for example using a diimide condensing reagent such as 1-(3-dimethylaminopropyl)-3-ethylcarbodiimide. Alternatively, in appropriate cases (for example when the heterocyclic group is a 1-piperidyl or 1-piperazinyl group) the heterocyclic group is initially reacted with phosgene to provide the N—COCl intermediate which is then reacted with the amine of formula II. All these reactions are quite conventional and conditions for their performance will be well known to those skilled in the art as will other possibilities and variations.

(e) Compounds of the formula (I) wherein $R^4$ is $—C(=N—R^6)R^7$ are again prepared from the amines of formula (II) by reacting with a compound of the formula:

wherein $R^6$ is as previously defined and $R^{10}$ is $SCH_3$, $NR_2$, or $NHCO(C_1–C_4$ alkyl) and, in the case where $R^{10}$ is $SCH_3$, reacting the product with a $C_1–C_4$ alkylamine, dialkylamino-alkylamine, or heterocyclic amine.

The reaction between the amine (II) and the compound of formula (IV) is generally performed by heating the reactants together, in more or less equimolar proportions, in a reaction-inert organic solvent. A period of several hours heating under reflux in ethanol is generally found to be sufficient and the product is then simply isolated by removal of the solvent and purified by conventional procedures.

In the case where $R^6$ is H and $R^{10}$ is $NH_2$ the compound of formula (IV) is S-methyl-isothiourea which is conveniently reacted as its sulphate to provide the unsubstituted guanidines of formula (I) wherein $R^4$ is $C(=NH)NH_2$. This can be further reacted with a sulphonyl halide to give the compounds where $R^6$ is $SO_2(C_1–C_4$ alkyl) or $SO_2$-aryl.

In the case where $R^{10}$ is $SCH_3$ the resulting methylisothiourea is further reacted with an appropriate amine, usually by adding the reactants to ethanol at room temperature, typically for an overnight period, and the product is isolated by evaporation of the solvent and purified by conventional methods, e.g. by crystallisation. The methylisothiourea intermediate may also be generated from the thiourea of formula (I) (where $R^3$ is H and $R^4$ is C(=S)$NH_2$) by reacting with methyl iodide. The resulting S-methylisothiouronium salt may then be reacted with the amine component as before.

(f) Compounds of the formula (I) wherein $R^4$ is $SO_2$—$R^5$ are again also prepared from the amines of formula (II) by reacting with sulphamide, or a sulphonyl chloride of the formula:

$$ClSO_2R^{11} \qquad (V)$$

wherein $R^{11}$ is $C_1$–$C_4$ lower alkyl, NH($C_1$–$C_4$ alkyl), NH($C_3$–$C_6$ cycloalkyl), N($C_1$–$C_4$ alkyl)$_2$, NH-aryl, NHCO-aryl or a heterocyclic, NH heterocyclic or NHCO-heterocyclic group.

The reaction with sulphamide is typically achieved by heating the amine and sulphamide, in excess, under reflux in a reaction-inert organic solvent, e.g. dioxan. After a period of one or two hours the product is isolated and purified in a conventional manner. The reaction with a sulphonyl chloride of formula (V) is again performed in a conventional manner by adding the sulphonyl chloride to the amine in an inert organic solvent, e.g. dichloromethane, in the presence of an organic base, e.g. triethylamine. The reaction is generally complete after several hours at room temperature and the product is isolated and purified using conventional methods.

Preparation of the starting amines of formula (II) is described in the specification to our European patent application No. 89167. The various reactants of formula III, IV, V and $R^9CO_2H$, etc., are generally known compounds, either commercially available or they may be prepared by conventional methods in accordance with literature precedents.

The ability of the compounds of the invention to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force transducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and, after 45 minutes the test is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds will generally be in the range of from 2–100 mg daily for an average adult patient (70 kg). Thus for a typical adult patient, individual tablets or capsules contain from 1 to 10 mg of active compound, in a suitable pharmaceutically acceptable vehicle or carrier. Dosages for intravenous administration would typically be within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

Thus in a further aspect the invention provides a pharmaceutical composition comprising a compound of the formula (I), or a pharmaceutically acceptable acid addition salt thereof, together with a pharmaceutically acceptable diluent or carrier.

The invention also provides a method of protecting the heart from the deleterious effects of ischaemia, which comprises administering an effective amount of a compound of the formula (I) or pharmaceutically acceptable acid addition salt thereof, or pharmaceutical composition as defined above.

The invention also includes a method of treating hypertension which comprises administering an antihypertensive amount of a compound of the formula (I) or pharmaceutically acceptable acid addition salt thereof, or pharmaceutical composition as defined above.

The following examples illustrate the invention:

EXAMPLE 1

1-<2-{[4-(2-Chlorophenyl)-3-ethoxycarbonyl-5-methoxycarbonyl-6-methyl-1,4-dihydropyridin-2-yl]methoxy}ethyl>-3-methylurea Methyl isocyanate (0.5 ml) was added to a solution of 2-(2-aminoethoxymethyl)-4-(2-chlorophenyl)-3-ethoxycarbonyl-5-methoxycarbonyl-6-methyl-1,4-dihydropyridine (0.41 g) in dichloromethane (50 ml) and the mixture stirred at room temperature for 2 hours and then evaporated. The residue was triturated with diethyl ether and the solid collected, washed with diethyl ether, and dried to give the title compound (0.40 g), m.p. 75°–90° C. decomp. Found: C,56.81; H,6.14; N,9.21. $C_{22}H_{28}ClN_3O_6$ requires C,56.71; H,6.06; N,9.02%.

EXAMPLES 2–9

The following compounds were prepared by the method described in Example 1 from 2-(2-aminoethoxymethyl)-4-(2-chlorophenyl or 2,3-dichlorophenyl)-3-ethoxycarbonyl-5-methoxycarbonyl-6-methyl-1,4-dihydropyridine, or the appropriate substituted amine where $R^3$ is $CH_3$ or $CH_2CO_2CH_3$, and the appropriate isocyanate.

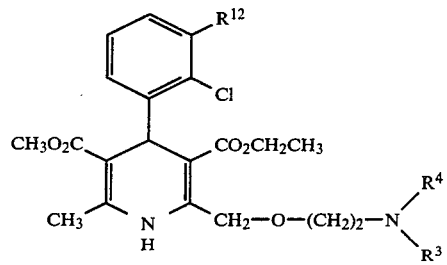

| Example No. | R¹² | R³ | R⁴ | m.p. (°C.) | Analysis % (Theoretical in brackets) C | H | N |
|---|---|---|---|---|---|---|---|
| 2 | H | CH₃ | CONHCH₃ | 160–162 | 57.56 (57.55 | 6.45 6.30 | 8.55 8.76) |
| 3 | H | H | CONHCH(CH₃)₂ | 164 | 58.19 (58.35 | 6.58 6.53 | 8.60 8.51) |
| 4 | H | CH₃ | CONHCH₂CO₂CH₂CH₃ | 116–120 | 56.18 (56.57 | 6.27 6.21 | 8.10 7.61) |
| 5 | H | CH₃ | CONHCOC₆H₅ | — | 61.33 (61.10 | 5.52 5.66 | 7.48 7.37) |
| 6 | H | CH₂CO₂CH₃ | CONHCH₃ | 174–176 | 55.95 (55.81 | 6.28 6.00 | 7.58 7.81) |
| 7 | H | H | CONHC₆H₅ | 156 | 57.51 (57.66 | 5.21 5.20 | 7.38 7.47) |
| 8 | Cl | CH₂CO₂CH₃ | CONHCH₅ | 118–120 | 52.45 (52.22 | 5.45 5.41 | 7.34 7.12) |
| 9 | H | CH₂CN | CONHCH₃ | 113–115 | 56.78 (57.10 | 5.98 5.75 | 11.40 11.10) |

EXAMPLE 10

1-<2-{[4-(2-Chlorophenyl)-3-ethoxycarbonyl-5-methoxycarbonyl-6-methyl-1,4-dihydropyridin-2-yl]methoxy}ethyl>-1-(methoxycarbonylmethyl)urea A solution of potassium cyanate (0.24 g), methyl 2-<2-{[4-(2-chlorophenyl)-3-ethoxycarbonyl-5-methoxycarbonyl-6-methyl-1,4-dihydropyridin-2-yl]methoxy}ethylamino>acetate (0.96 g) and acetic acid (0.36 g) in dioxane (10 ml) and water (10 ml) was stirred at room temperature for 70 minutes and then evaporated. The residue was partitioned between water and ethyl acetate and the organic layer separated, dried (Na₂SO₄) and evaporated. The residue was triturated with ethyl acetate and the resulting solid collected and dried to give the title compound (0.77 g), m.p. 166°–169° C. Found: C,54.65; H,5.78; N,8.13. C₂₄H₃₀ClN₃O₈ requires C,55.01; H,5.77; N,8.02%.

EXAMPLES 11–13

The following compounds were prepared by the method described in Example 10 from potassium cyanate and the appropriate 2-(2-aminoethoxymethyl)-1,4-dihydropyridine or the corresponding substituted derivative of formula (I) wherein R⁴ is hydrogen and R³ is as defined below.

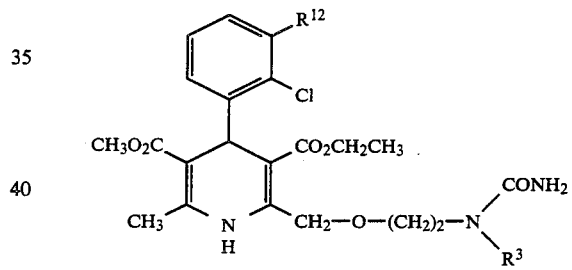

| Example No. | R¹² | R³ | m.p. (°C.) | Analysis % (Theoretical in brackets) C | H | N |
|---|---|---|---|---|---|---|
| 11 | H | H | 180–182 | 55.57 (55.81 | 5.79 5.76 | 9.20 9.30) |
| 12 | Cl | CH₂CO₂CH₃ | 176–178 | 51.15 (51.61 | 5.11 5.19 | 7.54 7.59) |
| 13 | H | CH₂CN | 190–191 | 56.34 (56.27 | 5.80 5.50 | 10.99 11.42) |

EXAMPLE 14

3-(Carbamoylmethyl)-1-<2-{[4-(2-chlorophenyl)-3-ethoxycarbonyl-5-methoxycarbonyl-6-methyl-1,4-dihydropyridin-2-yl]methoxy}ethyl>-1-methylurea 1->2-{[4-(2-Chlorophenyl)-3-ethoxycarbonyl-5-methoxycarbonyl-6-methyl-1,4-dihydropyridin-2-yl]methoxy}ethyl>-3-ethoxycarbonylmethyl-1-methylurea (0.44 g) was stirred in a mixture of ethanol (15 ml) and concentrated ammonium hydroxide (10 ml) for 24 hours and then evaporated. The residues was partitioned between chloroform and water and the organic layer dried (Na₂SO₄) and evaporated. The residue was triturated with diethyl ether/ethyl acetate and the resulting solid was collected, washed with diethyl ether, and dried to give the title compound (0.23 g), m.p. 142°–143° C. Found: C,54.85; H,5.97; N,10.58. $C_{24}H_{31}ClN_4O_7$ requires C,55.12; H,5.97; N,10.71%.

EXAMPLE 15

3-Carboxymethyl-1-<2-{[4-(2-chlorophenyl)-3-ethoxycarbonyl-5-methoxycarbonyl-6-methyl-1,4-dihydropyridin-2-yl]methoxy}ethyl>-1-methylurea 1M Aqueous sodium hydroxide solution (2 ml) was added dropwise over 5 minutes to a stirred, ice-cooled solution of 1-<2-{[4-(2-chlorophenyl)-3-ethoxycarbonyl-5-methoxycarbonyl-6-methyl-1,4-dihydropyridin-2-yl]methoxy}ethyl>-3-ethoxycarbonylmethyl-1-methylurea (0.44 g) in dioxane (20 ml). The mixture was stirred at room temperature for 4 hours and then evaporated. The residue was dissolved in water, washed with diethyl ether, acidified with 2M hydrochloric acid, and extracted into chloroform. The chloroform layer was dried ($MgSO_4$) and evaporated. The residue was triturated with diethyl ether/ethyl acetate and the resulting solid was collected, washed with diethyl ether, and dried to give the title compound (0.10 g) as a gum. Found: C,54.76; H,5.77; N,8.14. $C_{24}H_{30}ClN_3O_8$ requires C,55.01; H,5.79; N,8.02%.

EXAMPLE 16

A. Preparation of 2-(4-aminobutoxy)methyl-4-(2-chlorophenyl)-3-ethoxycarbonyl-5-methoxycarbonyl-6-methyl-1,4-dihydropyridine A solution of 4-azidobutanol (6.8 g) in tetrahydrofuran (100 ml) was added dropwise over 30 minutes to a suspension of sodium hydride (5.4 g; 60% dispersion in oil) in tetrahydrofuran (100 ml). The mixture was stirred at room temperature for 30 minutes and then treated with a solution of ethyl 4-chloroacetoacetate (9.7 g) in tetrahydrofuran (150 ml) dropwise over 30 minutes. The mixture was stirred at room temperature for 16 hours, poured into water and the pH adjusted to 3–4 with 2M hydrochloric acid. The aqueous solution was extracted with ethyl acetate (3×200 ml) and the organic layer was dried ($MgSO_4$) and evaporated to give an oil which was taken up in acetonitrile and washed with petrol. The solvent was evaporated to dryness and the residue was chromatographed on silica eluting with a mixture of petrol and methylene chloride. Fractions containing the product were evaporated to give ethyl 4-(4-azidobutoxy)acetoacetate as a yellow oil (4.5 g). Methyl 3-aminocrotonate (2.2 g) and 2-chlorobenzaldehyde (2.7 g) in methanol (50 ml) were added and the mixture was heated under reflux for 5 hours and then evaporated. The residue was chromatographed on silica eluting with a mixture of petrol and ethyl acetate to give 2-(4-azidobutoxy)methyl-4-(2-chlorophenyl)-3-ethoxycarbonyl-5-methoxycarbonyl-6-methyl-1,4-dihydropyridine (5.9 g) as a yellow oil. The product was taken up in methanol (70 ml) and stirred at room temperature for 16 hours under 1 atmosphere of hydrogen in the presence of 5% palladium on calcium carbonate catalyst (2.0 g). The reaction mixture was filtered and concentrated. The residue was treated with a solution of fumaric acid (1.0 g) in methanol. The resulting precipitate was collected, treated with 2M ammonium hydroxide and extracted with methylene chloride (2×25 ml). The organic layer was washed with water, dried ($MgSO_4$), filtered and evaporated to give 2-(4-aminobutoxy)methyl-4-(2-chlorophenyl)-3-ethoxycarbonyl-5-methoxycarbonyl-6-methyl-1,4-dihydropyridine (2.2 g) as a yellow oil. The product was used in the next stage without further purification.

B. 4-(2-Chlorophenyl)-3-ethoxycarbonyl-5-methoxycarbonyl-6-methyl-2-(4-[N-methylcarbamoyl]aminobutoxymethyl)-1,4-dihydropyridine, hemi-hydrate Methyl isocyanate (0.25 ml) was added to a solution of 2-(4-aminobutoxy)methyl-4-(2-chlorophenyl)-3-ethoxycarbonyl-5-methoxycarbonyl-6-methyl-1,4-dihydropyridine (0.1 g) in dry methylene chloride (5 ml) and the mixture stirred at room temperature for 14 hours. The solvent was evaporated and the residue was chromatographed on silica eluting with methylene chloride containing 5% methanol by volume. Fractions containing the product were combined and evaporated to give an oil which crystallised when triturated with diethyl ether to afford the title compound (0.05 g), m.p. 126°–126.5° C. Found: C,57.4; H,6.6; N,8.5. $C_{24}H_{23}ClN_3O_6.0.5H_2O$ requires C,57.3; H,6.4; N,8.35%.

EXAMPLE 17

4-(2-Chlorophenyl)-3-ethoxycarbonyl-5-methoxycarbonyl-6-methyl-2-[2-(thioureido)ethoxymethyl]-1,4-dihydropyridine (A) Thiophosgene (0.9 ml) was added to a stirred mixture of 2-(2-aminoethoxymethyl)-4-(2-chlorophenyl)-3-ethoxycarbonyl-5-methoxycarbonyl-6-methyl-1,4-dihydropyridine (4.08 g) and powdered $CaCO_3$ (3 g) in methylene chloride (25 ml) and water (35 ml). The mixture was stirred overnight at room temperature, filtered and partitioned between 2M hydrochloric acid and methylene chloride. The organic layer was washed with water, dried ($Na_2CO_3$), filtered and evaporated to give the isothiocyanate intermediate as a solid which was used directly for the next stage of the reaction without further purification.

(B) The isothiocyanate (4 g) was heated in ethanolic ammonia solution for 2½ hours. The precipitate was filtered and recrystallised from a mixture of ethanol and methylene chloride (5:1) to give the title compound, m.p. 203.5°–204.5° C. Found: C,53.3; H,5.5; N,8.6. $C_{21}H_{26}ClN_3O_5S$ requires C,53.8; H,5.6; N,8.9%.

EXAMPLE 18

4-(2-Chlorophenyl)-3-ethoxycarbonyl-5-methoxycarbonyl-6-methyl-2-[(2-N-methylthioureido)ethoxymethyl]-1,4-dihydropyridine was prepared by the method described in Example 17(B) but refluxing the isothiocyanate in ethanolic methylamine solution for 2 hours. The product solidified on trituration with diethyl ether, m.p. 138°–140° C. Found: C,54.24; H,5.79; N,8.72. $C_{22}H_{28}ClN_3O_5S$ requires C,54.82; H,5.86; N,8.72%.

EXAMPLE 19

4-(2,3-Dichlorophenyl)-3-ethoxycarbonyl-5-methoxycarbonyl-6-methyl-2-[2-(thioureido)ethoxymethyl]-1,4-dihydropyridine The title compound was prepared as described in Example 17 but starting with the corresponding 4-(2,3-dichlorophenyl)-1,4-dihydropyridine derivative, m.p. 198° C. Found: C,50.28; H,5.07; N,8.72. $C_{21}H_{25}Cl_2N_3O_5S$ requires C,50.20; H,5.02; N,8.30%.

EXAMPLE 20

3-(Carbamoylmethyl)-1-<2-{[4-(2-chlorophenyl)-3-ethoxycarbonyl-5-methoxycarbonyl-6-methyl-1,4-dihydropyridin-2-yl]methoxy}ethyl>urea A mixture of 2-{2-[(1-imidazolylcarbonyl)amino]ethoxy}methyl-4-(2-chlorophenyl)-3-ethoxycarbonyl-5-methoxycarbonyl-6-methyl-1,4-dihydropyridine (0.98 g) (prepared from the 2-(2-aminoethoxymethyl)dihydropyridine derivative and N,N'-carbonyldiimidazole), glycinamide hydrochloride (0.22 g) and N-methylmorpholine (0.44 g) in acetonitrile (10 ml) was stirred at room temperature for 22 hours and then evaporated to dryness. The residue was chromatographed on silica eluting with hexane containing 30% by volume of dichloromethane, followed by dichloromethane containing from 0 to 1% by volume of methanol. Appropriate fractions were combined and evaporated to give the title compound (0.25 g). m.p. 114°–116° C. Found: C,53.95; H,5.85; N,10.80. $C_{23}H_{29}ClN_4O_7$ requires C,54.28; H,5.70; N,11.01%.

EXAMPLE 21–24

The following compounds were prepared by the method described in Example 20 from 2-{2-[(1-imidazolylcarbonyl)amino]ethoxy}methyl-4-(2-chlorophenyl)-3-ethoxycarbonyl-5-methoxycarbonyl-6-methyl-1,4-dihydropyridine and the appropriate amine or hydrazine.

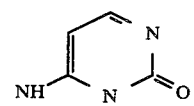

| Example No. | $R^5$ | m.p.(°C.) | C | H | N |
|---|---|---|---|---|---|
| 21 | NHCH₂CH₂NH₂ | 90 (decomp) | 52.35 (52.30 | 6.31 5.81 | 9.10 9.04) |
| 22 | 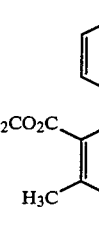 | 140–143 | 53.54 (53.24 | 5.04 5.32 | 11.84 12.42) |
| 23 | NHNH₂ | 144–146 | 54.02 (54.02 | 6.04 5.82 | 11.63 12.00) |
| 24 | NHNHCO₂CH₂CH₃ | 158–160 | 35.05 (35.48 | 5.87 5.80 | 10.65 10.40) |

EXAMPLE 25

4-(2-Chlorophenyl)-3-ethoxycarbonyl-5-methoxycarbonyl-6-methyl-2-[2-(3-pyridylcarbonylamino)ethoxymethyl]-1,4-dihydropyridine 1-(3-Dimethylaminopropyl)-3-ethylcarbodiimide hydrochloride (0.42 g) was added to an ice-cooled solution of 2-(2-aminoethoxymethyl)-4-(2-chlorophenyl)-3-ethoxycarbonyl-5-methoxycarbonyl-6-methyl-1,4-dihydropyridine (0.41 g), nicotinic acid (0.14 g) and 1-hydroxybenzotriazole hydrate (0.17 g) in dichloromethane (40 ml). The mixture was stirred with ice-cooling for 15 minutes, treated with N-methylmorpholine (0.61 g) and stirred at room temperature for 16 hours. The solution was then diluted with dichloromethane, washed successively with water, 2N hydrochloric acid, water, 10% aqueous sodium carbonate solution, and water, dried (Na₂SO₄) and evaporated. The residue was chromatographed on silica (t.l.c. grade, Merck Kieselgel 60H (Trade Mark) 8 g) eluting with dichloromethane plus 0–5% methanol. Appropriate fractions were combined and evaporated. The residue was triturated with diethyl ether and the resulting solid collected, washed with diethyl ether and dried to give the title compound (0.29 g), m.p. 81°–84° C. Found: C. 61.01; H, 5.48; N, 8.23. $C_{26}H_{28}ClN_3O_6$ requires C, 60.76; H, 5.49; N, 8.18%.

EXAMPLES 26–29

The following compounds were prepared by the method described in Example 25 from 2-(2-aminoethoxymethyl) or 2-(2-methylaminoethoxymethyl)-4-(2-chlorophenyl)-3-ethoxycarbonyl-6-methoxycarbonyl-6-methyl-1,4-dihydropyridine and the appropriate carboxy substituted heterocyclic compound.

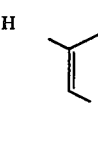

| Example No. | $R^3$ | $R^5$ | m.p. (°C.) | C | H | N |
|---|---|---|---|---|---|---|
| 26 | H | 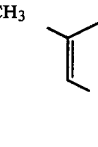 | 117–118 | 58.54 (58.31 | 5.36 5.28 | 10.67 10.88) |
| 27 | H | 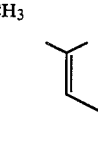 | 125–130 decomp. | 59.35 (58.92 | 5.78 5.33 | 7.70 7.93) |
| 28 | CH₃ | | 74–81 | 58.15 (57.91 | 5.51 5.40 | 7.40 7.50) |
| 29 | CH₃ | | 220–240 decomp. | 56.13 (55.67 | 5.19 5.21 | 9.85 9.99) |

EXAMPLE 30

4-(2,3-Dichlorophenyl)-3-ethoxycarbonyl-2-[(N-formyl)aminoethoxy methyl]-5-methoxycarbonyl-6-methyl-1,4-dihydropyridine Formic acetic anhydride (15 ml; prepared by heating a mixture of formic acid (5 ml) and acetic anhydride (10 ml) at 50°–60° C. for 1 hour) was added over 10 minutes to a stirred, ice-cooled solution of 2-(2-aminoethoxymethyl)-4-(2,3-dichlorophenyl)-3-ethoxycarbonyl-5-methoxycarbonyl-6-methyl-1,4-dihydropyridine (4.4 g) in tetrahydrofuran (30 ml). The mixture was stirred at room temperature for 1.5 hours and then evaporated. The residue was dissolved in dichloromethane and the solution washed with 10% aqueous sodium carbonate solution, dried ($Na_2SO_4$), and evaporated. The residual solid was collected, washed with diethyl ether and dried to give the title compound as a hemihydrate (4.0 g), m.p. 178°–181° C. Found: C, 52.69; H, 5.05; N, 6.06. $C_{21}H_{24}Cl_2N_2O_6.0.5H_2O$ requires C, 52.51; H, 5.25; N, 5.83%.

EXAMPLES 31–33

The following examples were prepared by the method described in Example 30 from the corresponding 4-(2-chlorophenyl)-1,4-dihydropyridine derivative using formic/acetic anhydride, acetic anhydride or trifluoroacetic anhydride respectively:

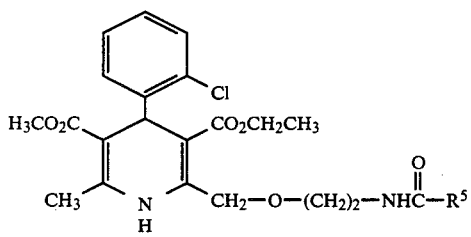

| Example No. | $R^5$ | m.p. (°C.) | C | H | N |
|---|---|---|---|---|---|
| 31 | H | 164–166 | 56.51 (56.57) | 5.82 5.88 | 6.04 (6.29) |
| | | | This compound is a hemihydrate | | |
| 32 | $CH_3$ | 97–99 | 59.00 (58.60) | 6.16 6.04 | 6.24 (6.21) |
| 33 | $CF_3$ | 141–143 | 52.41 (52.33) | 4.83 4.79 | 5.50 (5.56) |

EXAMPLE 34

4-(2-Chlorophenyl)-3-ethoxycarbonyl-5-methoxycarbonyl-6-methyl-2-[2-(4-methylpiperazin-1-ylcarbonylamino)ethoxymethyl]-1,4-dihydropyridine A solution of N-methylpiperazine in toluene (5 ml) and triethylamine (1 ml) was added dropwise to a 12.5% (by weight) solution of phosgene in toluene (7.5 ml) at −30° C. The solution was allowed to warm to room temperature over 1.5 hours and then purged with nitrogen to remove excess phosgene. 2-(2-Aminoethoxymethyl)-4-(2-chlorophenyl)-3-ethoxycarbonyl-5-methoxycarbonyl-6-methyl-1,4-dihydropyridine was then added and the mixture allowed to stir at room temperature for 17 hours. After evaporation to dryness, the resultant oil was partitioned between 5% aqueous sodium carbonate and diethyl ether. The combined organic liquors were dried ($MgSO_4$), filtered and evaporated to give 0.7 g of a colourless oil. This oil was chromatographed on Kieselgel 60 (Trade Mark) (3 g), eluting with ethyl acetate to give 0.2 g of a white solid. Crystallisation from ethyl acetate afforded the pure title compound (0.13 g), m.p. 78°–80° C. Found: C, 58.36; H, 6.59; N, 10.47%. $C_{26}H_{35}ClN_4O_6$ requires C, 58.35; H, 6.64; N, 10.41%.

EXAMPLE 35

4-(2-Chlorophenyl)-3-ethoxycarbonyl-2-[2-(imidazolidin-2-on-1-ylcarbonylamino)ethoxymethyl]-5-methoxycarbonyl-6-methyl-1,4-dihydropyridine To a solution of 2-(2-aminoethoxymethyl)-4-(2-chlorophenyl)-3-ethoxycarbonyl-5-methoxycarbonyl-6-methyl-1,4-dihydropyridine (1.0 g) in a mixture of chloroform (dried over alumina) (20 ml) and triethylamine (2 ml) was added imidazolidin-2-on-1-yl carbonyl chloride (0.36 g) in one portion and the mixture stirred at room temperature for 18 hours. After evaporation to dryness, the resultant oil was partitioned between 5% aqueous sodium carbonate and methylene chloride. The combined organic liquors were dried ($MgSO_4$), filtered and evaporated to give 0.7 g of a yellow oil which crystallised from diisopropyl ether on standing to give pure title compound, (0.4 g), m.p. 145° C. Found: C, 54.94; H, 5.62; N, 10.62. $C_{24}H_{29}ClN_4O_7$ requires C, 55.33; H, 5.61; N, 10.76%.

EXAMPLE 36

3-<2-{[4-(2-Chlorophenyl-3-ethoxycarbonyl-5-methoxycarbonyl-6-methyl-1,4-dihydropyridin-2-yl]methoxy}ethyl>-2-cyano-1-methylguanidine (A) A solution of 2-(2-aminoethoxymethyl)-4-(2-chlorophenyl)-3-ethoxycarbonyl-5-methoxycarbonyl-6-methyl-1,4-dihydropyridine (0.82 g) and di(methylthio)methylidinoiminonitrile (0.29 g) in ethanol (50 ml) was heated under reflux for 2 hours and then evaporated. The residue was triturated with diethyl ether and the resulting solid collected, washed with ether, and dried to give 1-> 2-{[4-(2-chlorophenyl)-3-ethoxycarbonyl-5-methoxycarbonyl-6-methyl-1,4-dihydropyridin-2-yl]methoxy}ethyl>-3-cyano-2-methylisothiourea (0.96 g), m.p. 177°–179° C. Found: C, 54.34; H, 5.42; N, 11.18. $C_{23}H_{27}ClN_4O_5S$ requires C, 54.49; H, 5.37; N, 11.05%.

(B) The product from (A) (0.40 g) in 33% (by weight) ethanolic methylamine solution (10 ml) was stirred for 18 hours and then evaporated. The residue was recrystallised from ethanol to give the title compound (0.25 g), m.p. 188°–190° C. Found: C, 56.66; H, 5.53; N, 14.08, $C_{23}H_{28}ClN_2O_5$ requires C, 56.38; H, 5.76; N, 14.29%.

EXAMPLE 37

2-Cyano-3-<2-{[4-(2,3-dichlorophenyl)-3-ethoxycarbonyl-S-methoxycarbonyl-6-methyl-1,4-dihydropyridin-2-yl]methoxy}ethyl>-1-methylguanidine was prepared by the method described in Example 36B from 3-cyano-1-<2-{[4-(2,3-dichlorophenyl)-3-ethoxycarbonyl-5-methoxycarbonyl-6-methyl-1,4-dihydropyridin-2-yl]methoxy}ethyl>-2-methylisothiourea. The product was obtained as a monohydrate which had m.p. 175° C. Found: C, 50.62; H, 5.12; N, 12.81. $C_{23}H_{27}Cl_2N_5O_5.H_2O$ requires C, 50.92; H, 5.38; N, 12.91%.

EXAMPLES 38–40

The following compounds were prepared by the method described in Example 36(A) from 2-(2-aminoethoxymethyl)-4-(2-chlorophenyl)-3-ethoxycarbonyl-5-methoxycarbonyl-6-methyl-1,4-dihydropyridine and the appropriate compound of formula (IV).

[Structure: 4-(2-chlorophenyl)-1,4-dihydropyridine with $CH_3O_2C$ and $CO_2CH_2CH_3$ groups, $CH_3$, NH, and $CH_2$—O—$(CH_2)_2$—N($R^3$)($R^4$)]

| Example No. | $R^3$ | $R^4$ | m.p. (°C.) | Analysis % (Theoretical in brackets) | | |
|---|---|---|---|---|---|---|
| | | | | C | H | N |
| 38 | H | —C(=N.CO$_2$CH$_3$)NH$_2$ | 115–116 | 53.95 (54.27 | 5.74 5.74 | 11.19 11.01) |
| 39 | H | —C(=N.COCH$_3$)NH.COCH$_3$ | 146–147 | 56.00 (56.12 | 5.86 5.84 | 10.15 10.47) |
| 40 | H | —C(=N—NO$_2$)NH$_2$ | 122–124 | 50.83 (50.96 | 6.10 5.91 | 12.66 12.92) |

EXAMPLE 41

1-<2-{[4-(2-Chlorophenyl)-3-ethoxycarbonyl-5-methoxycarbonyl-6-methyl-1,4-dihydropyridin-2-yl]methoxy}ethyl>-2-cyano-3-(2-dimethylamino)ethylguanidine was prepared by the method described in Example 36(B) but using ethanolic N,N-dimethylethylenediamine instead of ethanolic methylamine. The product had m.p. 202°–204° C. decomp. Found: C, 56.67; H, 6.51; N, 15.58. C$_{26}$H$_{35}$ClN$_6$O$_5$ requires C, 57.08; H, 6.45; N, 15.36.

EXAMPLE 42

4-(2,3-Dichlorophenyl)-3-ethoxycarbonyl-5-methoxycarbonyl-6-methyl-2-{2-[N-(2-thiazolyl)guanidino]ethoxymethyl}-1,4-dihydropyridine hydrate (A) 4-(2,3-Dichlorophenyl)-3-ethoxycarbonyl-5-methoxycarbonyl-6-methyl-2-[2-(thioureido)ethoxymethyl]-1,4-dihydropyridine (4.2 g) was dissolved in a mixture of methanol (25 ml) and methylene chloride (25 ml) and stirred at room temperature. Methyl iodide (1.2 g) was added and the solution stirred for 40 hours. After evaporation to dryness, trituration with diethyl ether gave the intermediate S-methylisothiouronium hydriodide as a solid which was used directly for the next stage of the reaction without further purification.

(B) The S-methylisothiouronium hydriodide (3.3 g) and 2-aminothiazole (0.64 g) were suspended in a mixture of n-butanol (25 ml) and triethylamine (3.3 g) and the mixture stirred at reflux for 5 hours. After evaporation to dryness, the residual oil was partitioned between 5% aqueous sodium bicarbonate (50 ml) and methylene chloride (3×75 ml). The combined organic extracts were dried (MgSO$_4$), filtered and evaporated to give a dark brown oil (4.2 g). The residual oil was chromatographed on silica eluting with toluene containing an increasing proportion of ethylacetate. The product was finally crystallised from toluene to give the title compound, m.p. 116°–119° C. Found: C, 49.21; H, 4.67; N, 12.15. C$_{24}$H$_{27}$Cl$_2$N$_5$O$_5$S.H$_2$O. requires C, 49.15; H, 4.98; N, 11.94%.

EXAMPLE 43

4-(2,3-Dichlorophenyl)-3-ethoxycarbonyl-2-[2-(guanidino)ethoxymethyl]-5-methoxycarbonyl-6-methyl-1,4-dihydropyridine 2-(2-Aminoethoxymethyl)-4-(2,3-dichlorophenyl)-3-ethoxycarbonyl-5-methoxycarbonyl-6-methyl-1,4-dihydropyridine (5.0 g) and S-methylisothiourea sulphate (3.45 g) was suspended in n-propanol (120 ml) and triethylamine (30 ml) and refluxed for 17 hours. After evaporation to dryness, the residual oil was partitioned between aqueous sodium bicarbonate and methylene chloride. The organic layer was dried (MgSO$_4$), filtered and evaporated. The resultant beige solid was triturated with hexane to give the title compound (4.1 g), N.M.R. (CDCl$_3$, 60 MHz): 3H 1.15(t), 3H 3.55(s), 4H 3.7(m), 2H 4.0(q), 2H 4.7(s), 1H 5.45(s), 8H 7.25(m).

EXAMPLE 44

4-(2,3-Dichlorophenyl)-3-ethoxycarbonyl-5-methoxycarbonyl-6-methyl-2-{2-[N-(N'-phenyl-sulphonyl)-guanidinyl]ethoxymethyl}-1,4-dihydropyridine 4-(2,3-Dichlorophenyl)-3-ethoxycarbonyl-2-[2-(N-guanidino)ethoxymethyl]-5-methoxycarbonyl-6-methyl-1,4-dihydropyridine (1.19 g) was added to 10% aqueous sodium hydroxide solution (40 ml), followed by benzenesulphonyl chloride (0.9 g). The mixture was shaken vigorously for 15 minutes and stirred at room temperature for a further 1 hour. The resultant mixture was extracted with diethyl ether (2×25 ml) and then methylene chloride (3×75 ml). The combined methylene chloride liquors were dried (MgSO$_4$), filtered and evaporated and the residual yellow solid chromatographed on silica eluting with 50% by volume ethyl acetate in toluene. Crystallisation of the product from petroleum ether (b.p. 100°–120° C.) and ethyl acetate afforded the title compound, 0.19 g, m.p. 153°–154°. Found: C, 52.22; H, 5.02; N, 8.79. C$_{27}$H$_{30}$Cl$_2$N$_4$O$_7$S requires C, 51.84; H, 4.83; N, 8.96%.

EXAMPLE 45

4-(2-Chlorophenyl)-3-ethoxycarbonyl-5-methoxycarbonyl-2-{2-[(N-methanesulphonyl)-N-methylamino]ethoxymethyl}-6-methyl-1,4-dihydropyridine Methanesulphonyl chloride (0.144 g) was added to a solution of 4-(2-chlorophenyl)-3-ethoxycarbonyl-5-methoxycarbonyl-6-methyl-2-[2-(methylamino)ethoxymethyl]-1,4-dihydropyridine (0.50 g) and triethylamine (0.126 g) in dichloromethane (15 ml). The mixture was stirred at room temperature for 1 hour, poured into ice-water and the layers separated. The organic layer was washed with water, dried (Na$_2$SO$_4$) and evaporated. Scratching the residual oil afforded a solid which was recrystallised from methanol to give the title compound (0.33 g), m.p. 93°–95° C. Found: C, 53.32; H, 5.97; N, 5.64. C$_{22}$H$_{29}$ClN$_2$O$_7$S requires C, 53.32; H, 5.92; N, 5.71%.

EXAMPLE 46

4-(2-Chlorophenyl)-3-ethoxycarbonyl-5-methoxycarbonyl-6-methyl-2-{2-[(2-chloro-5-pyridyl)sulphonamido]ethoxymethyl}-1,4-dihydropyridine A solution of 2-(2-aminoethoxymethyl)-4-(2-chlorophenyl)-3-ethoxycarbonyl-5-methoxycarbonyl-6-methyl-1,4-dihydropyridine (409 mg) and triethylamine (202 mg) in dry dichloromethane (20 ml) was stirred under nitrogen and cooled in an ice-bath while a solution of 2-chloro-5-pyridinesulphonyl chloride (212 mg) in dry dichloromethane (10 ml) was added dropwise. The reaction mixture was allowed to warm to room temperature and stirring continued for a further 3 hours. The solvent was evaporated and the residue chromatographed on silica, eluting with dichloromethane. Appropriate fractions were combined and evaporated and the residue recrystallised from ethyl acetate to give the title compound (320 mg), m.p. 140°-140.5° C. Found: C, 51,27; H, 4.63; N, 7.25. C$_{25}$H$_{27}$Cl$_2$N$_3$O$_7$ requires C, 51.37; H, 4.66; N, 7.19%.

EXAMPLES 47–53

The following compounds were prepared following the general procedures described in Examples 45 or 46 starting with 2-(2-aminoethoxymethyl)-4-(2-chlorophenyl or 2,3-dichlorophenyl)-3-ethoxycarbonyl-5-methoxycarbonyl-6-methyl-1,4-dihydropyridine and the appropriate sulphonyl chloride.

| Example No. | R$^5$ | R$^{12}$ | m.p. (°C.) | Analysis % (Theoretical in brackets) C | H | N |
|---|---|---|---|---|---|---|
| 47 | 5-methyl-2-chloropyridyl | Cl | 195.5–198 | 48.34 (48.51 | 4.32 4.23 | 6.88 6.79) |
| 48 | 2-methylthienyl | Cl | 199–200.5 | 48.85 (48.89 | 4.40 4.45 | 4.29 4.75) |
| 49 | 4-methyl-2-acetamidothiazolyl | Cl | 153–156 | 47.46 (47.20 | 4.89 4.57 | 8.81 8.47) |
| 50 | 8-quinolinyl | Cl | 160–162 | 54.85 (54.89 | 4.51 4.61 | 6.62 6.62) |
| 51 | —NH—cyclopentyl | Cl | 151–152 | 51.05 (50.85 | 5.63 5.63 | 7.41 7.12) |
| 52 | —N(morpholino) | H | 155–157 | 51.56 (51.65 | 5.9 5.8 | 7.5 7.8) |
| 53 | —N(morpholino) | Cl | 169–170 | 48.9 (48.65 | 5.2 5.3 | 6.9 7.1) |

EXAMPLE 54

4-(2,3-Dichlorophenyl)-3-ethoxycarbonyl-5-methoxycarbonyl-6-methyl-2{2-[(2-(4-morpholino-5-pyridyl)-sulphonamido]ethoxymethyl}-1,4-dihydropyridine A solution of 4-(2,3-dichlorophenyl)-3-ethoxycarbonyl-5-methoxycarbonyl-6-methyl-2-{2-[(2-chloro-5-pyridyl)sulphonamido]-ethoxymethyl}-1,4-dihydropyridine (200 mg) in morpholine (2 ml) was heated on a steam bath for 6 hours.

The reaction mixture was evaporated to dryness and the residue partitioned between dichloromethane and water. The organic layer was separated, washed with water, dried over anhydrous magnesium sulphate and evaporated to give an orange gum. Chromatography on silica eluting with dichloromethane followed by dichloromethane containing 2% by volume of methanol gave the title compound (125 mg) which was recrystallised from ethyl acetate, m.p. 172.5°–173° C. Found: C, 52.04; H, 5.10; N, 8.48. $C_{29}H_{34}Cl_2N_4O_8$ requires C, 52.02; H, 5.12; N, 8.37%.

EXAMPLES 55 AND 56

The following compounds were prepared in a similar manner to Example 54 but using cyclopentylamine or N-methylpiperazine, respectively instead of morpholine.

| Example No. | $R^{15}$ | m.p. (°C.) | Analysis % (Theoretical in brackets) C | H | N |
|---|---|---|---|---|---|
| 55 | —NH—(cyclopentyl) | 180–182 | 53.96 (53.97 | 5.52 5.44 | 8.21 8.39) |
| 56 | —N(piperazinyl)N—CH₃ | 172–174.5 | 52.72 (52.78 | 5.42 5.46 | 10.08 10.26) |

EXAMPLE 57

2-{[4-(2-Chlorophenyl)-3-ethoxycarbonyl-5-methoxycarbonyl-6-methyl-1,4-dihydropyridin-2-yl]methoxy}ethylsulphamide A solution of 2-(2-aminoethoxy)methyl-4-(2-chlorophenyl)-3-ethoxycarbonyl-5-methoxycarbonyl-6-methyl-1,4-dihydropyridine (0.82 g) and sulphamide (0.96 g) in dioxane (30 ml) was heated under reflux for 70 minutes and then evaporated. The residue was partitioned between ethyl acetate and water and the organic layer dried ($Na_2SO_4$) and evaporated. The residue was triturated with diethyl ether and the resulting solid collected, washed with diethyl ether and dried to give the title compound (0.75 g), m.p. 150°–152° C. Found: C, 49.33; H, 5.35; N, 8.93. $C_{20}H_{26}ClN_3O_7S$ requires C, 49.23; H, 5.37; N, 8.61%.

EXAMPLE 58

2-{[4-(2,3-Dichlorophenyl)-3-ethoxycarbonyl-5-methoxycarbonyl-6-methyl-1,4-dihydropyridin-2-yl]methoxy}ethylsulphamide This compound was prepared as described above starting with the corresponding 4-(2,3-dichlorophenyl)-dihydropyridine. m.p. 89°–90° C. Found: C, 45.57; H, 4.89; N, 7.86. $C_{20}H_{25}Cl_2N_3O_7S$ requires C, 45.98; H, 4.79; N, 8.04.

EXAMPLE 59

1-<2-{[4-(2-Chlorophenyl)-3-ethoxycarbonyl-5-methoxycarbonyl-6-methyl-1,4-dihydropyridin-2-yl]methoxy}ethyl>-1-methyl sulphamide was prepared by the method described in Example 57 from 4-(2-chlorophenyl)-3-ethoxycarbonyl-5-methoxycarbonyl-6-methyl-2-[2-(N-methylamino)ethoxy]methyl-1,4-dihydropyridine. The product had m.p. 117°–120° C. Found: C, 50.66; H, 5.69; N, 8.22. $C_{21}H_{28}ClN_3O_7S$ requires C, 50.25; H, 5.62; N, 8.37%.

EXAMPLE 60

4-(2-Chlorophenyl)-3-ethoxycarbonyl-5-methoxycarbonyl-6-methyl-2-[2-(4-methyl-1-piperazinylsulphonylamino)ethoxymethyl]-1,4-dihydropyridine 2-(2-Aminoethoxymethyl)-4-(2-chlorophenyl)-3-ethoxycarbonyl-5-methoxycarbonyl-6-methyl-1,4-dihydropyridine (0.5 g) was dissolved in a mixture of chloroform (dried over alumina) (20 ml) and triethylamine (2 ml) and the mixture stirred at room temperature. 4-Methyl-1-piperazinylsulphonyl chloride (0.25 g) was added in one portion and the mixture stirred at room temperature for 17 hours. After evaporation to dryness, the resultant oil was partitioned between 5% aqueous sodium carbonate and methylene chloride. The organic layer was dried ($MgSO_4$), filtered and evaporated to give 0.3 g of a colourless oil, which was dissolved in diisopropyl ether (15 ml) and kept in a refrigerator for 14 days. The resultant crystals were collected by filtration to afford the title compound (0.1 g), m.p. 137°–139° C. Found: C, 52.58; H, 6.18; N, 9.81%. $C_{25}H_{35}ClN_4O_7S$ requires C, 53.03; H, 6.14; N, 9.20%.

EXAMPLE 61

4-(2-Chlorophenyl)-3-ethoxycarbonyl-2-[2-(2-furoylaminosulphonylamino)ethoxymethyl]-5-methoxycarbonyl-6-methyl-1,4-dihydropyridine To a solution of 2-(2-aminoethoxymethyl)-4-(2-chlorophenyl)-3-ethoxycarbonyl-5-methoxycarbonyl-6-methyl-1,4-dihydropyridine (0.5 g) in chloroform (dried over alumina) and triethylamine (2 ml) was added 2-furoylsulphamoyl chloride in one portion and the mixture stirred at room temperature for 17 hours. After evaporation to dryness, the resultant oil was partitioned between 5% aqueous sodium bicarbonate and methylene chloride. The combined organic liquors were dried ($MgSO_4$), filtered and evaporated to give 0.35 g of solid which was crystallised from diisopropyl ether to give pure title compound (0.2 g), m.p. 138° C. Found: C, 51.30; H, 5.23; N, 7.41. $C_{25}H_{28}ClN_3O_9S$ requires C, 51.59; H, 4.85; N, 7.22%.

EXAMPLE 62

Tablets are compounded from the following ingredients:

| | mg/tablet |
|---|---|
| Product of any one of Examples | 10 |
| Dicalcium phosphate | 120 |
| Magnesium stearate | 1.8 |
| Sodium lauryl sulphate | 0.2 |

EXAMPLE 63

Capsules are compounded from the following ingredients:

| | mg/capsule |
|---|---|
| Product of any one of Examples | 10 |
| Maize starch | 127 |
| Cellulose (microcrystalline) | 127 |
| Magnesium stearate | 5.4 |
| Sodium lauryl sulphate | 0.6 |

The ingredients are thoroughly blended, then filled into hard gelatine capsules of the appropriate size to contain the ingredients.

We claim:

1. A 1,4-dihydropyridine compound having the formula:

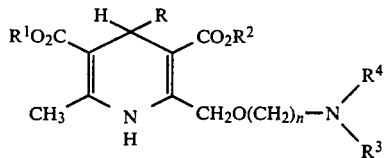

wherein R is 2,3-dichlorophenyl;
$R^1$ and $R^2$ are each independently $C_1$–$C_4$ alkyl;
n is 2; $R^3$ is H or $C_1$–$C_4$ alkyl; and
$R_4$ is a group of the formula

—$SO_2R^5$ wherein
$R^5$ is 2-chloropyrid-5-yl or 2-(4-methylpiperazin-1-yl)pyrid-5-yl and a pharmaceutically acceptable acid addition salt thereof.

2. A compound according to claim 1 wherein $R^1$ is $CH_3$ and $R^2$ is $C_2H_5$.

3. A compound according to claim 2 wherein $R^3$ is H or $CH_3$.

4. A compound according to claim 3 wherein $R^4$ is $SO_2R^5$ where $R^5$ is 2-(4-methylpiperazin-1-yl)pyrid-5-yl.

5. A 1,4-dihydropyridine compound having the formula

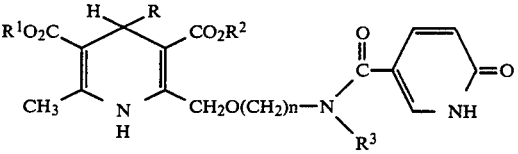

wherein R is 2-chlorophenyl;
$R^1$ and $R^2$ are each independently $C_1$–$C_4$ alkyl; n is 2; and $R^3$ is H or $C_1$–$C_4$ alkyl.

6. A method for treating hypertension in a mammal comprising administering to said mammal an antihypertensive effective amount of a compound according to claim 1 or 5.

* * * * *